(12) United States Patent
Ash

(10) Patent No.: US 11,998,672 B2
(45) Date of Patent: Jun. 4, 2024

(54) SLOTTED PERITONEAL ACCESS CATHETER

(71) Applicant: Stephen Richard Ash, Lafayette, IN (US)

(72) Inventor: Stephen Richard Ash, Lafayette, IN (US)

(*) Notice: Subject to any disclaimer, the term of this patent is extended or adjusted under 35 U.S.C. 154(b) by 177 days.

(21) Appl. No.: 16/207,276

(22) Filed: Dec. 3, 2018

(65) Prior Publication Data

US 2019/0231961 A1 Aug. 1, 2019

Related U.S. Application Data

(60) Provisional application No. 62/594,079, filed on Dec. 4, 2017.

(51) Int. Cl.
*A61M 1/28* (2006.01)
*A61M 25/00* (2006.01)
*A61M 25/01* (2006.01)

(52) U.S. Cl.
CPC .......... *A61M 1/285* (2013.01); *A61M 25/007* (2013.01); *A61M 25/0015* (2013.01); *A61M 25/0021* (2013.01); *A61M 2025/0188* (2013.01); *A61M 2210/1017* (2013.01)

(58) Field of Classification Search
CPC ............ A61M 25/007; A61M 25/0021; A61M 2025/0188; A61M 25/0032; A61M 1/285; A61M 25/0015; A61M 2210/1017; A61M 1/14; A61M 1/28; A61M 25/00; A61M 25/0067; A61M 25/0068; A61M 25/0043; A61M 25/0017; A61M 25/0023; A61M 25/01; A61M 25/0194; A61M 2025/0197; A61M 2025/0213; A61M 2025/0233;
(Continued)

(56) References Cited

U.S. PATENT DOCUMENTS 4,391,276 A * 7/1983 Lazarus ............. A61M 25/007
604/266
4,498,902 A 2/1985 Ash et al.
(Continued)

FOREIGN PATENT DOCUMENTS

DE 102006056049 A1 * 5/2008
EP 0284365 A2 * 9/1988 ............ A61M 1/008
(Continued)

OTHER PUBLICATIONS

ProQuest Dialog, English Machine Translation of FR 2240026, 8 pages (Year: 1975).*
(Continued)

*Primary Examiner* — Jason E Flick
(74) *Attorney, Agent, or Firm* — Tyler B. Droste; Gutwein Law

(57) ABSTRACT

Methods and design for a Slotted T-shaped PD Catheter are disclosed. The present invention includes a unique port design for peritoneal dialysis catheters that allows high outflow and inflow rates, with a minimum fluid velocity through the fluid entry ports. Features of this device include T-shaped catheter with subcutaneous tubing joining to an intraperitoneal portion that is essentially at right angles to the intraperitoneal tubing and slit shaped flow ports as opposed to round shaped flow ports.

13 Claims, 18 Drawing Sheets

(58) Field of Classification Search
CPC .......... A61M 25/02; A61M 2025/0286; A61M 25/04
See application file for complete search history.

(56) References Cited

U.S. PATENT DOCUMENTS

| | | | | |
|---|---|---|---|---|
| 4,650,463 | A * | 3/1987 | LeVeen | A61M 1/008 604/128 |
| 4,772,269 | A * | 9/1988 | Twardowski | A61M 1/285 604/175 |
| 4,935,004 | A * | 6/1990 | Cruz | A61M 1/285 604/530 |
| 5,141,499 | A * | 8/1992 | Zappacosta | A61M 1/285 604/175 |
| 5,322,519 | A * | 6/1994 | Ash | A61M 1/284 604/264 |
| 5,360,414 | A * | 11/1994 | Yarger | A61M 25/0043 604/264 |
| 5,752,939 | A * | 5/1998 | Makoto | A61M 1/285 604/523 |
| 7,223,263 | B1 * | 5/2007 | Seno | A61M 1/285 604/537 |
| 9,144,660 | B2 * | 9/2015 | Degen | A61M 1/285 |
| 2004/0034333 | A1 * | 2/2004 | Seese | A61M 1/285 604/523 |
| 2004/0210180 | A1 | 10/2004 | Altman | |
| 2005/0245900 | A1 | 11/2005 | Ash | |
| 2007/0225682 | A1 | 9/2007 | Ash et al. | |
| 2009/0018493 | A1 * | 1/2009 | Ash | A61M 1/285 604/29 |

FOREIGN PATENT DOCUMENTS

| | | | |
|---|---|---|---|
| FR | 2240026 A1 * | 3/1975 | ........ A61M 25/0108 |
| FR | 2248057 A2 * | 5/1975 | .......... A61M 1/0084 |
| JP | H08206219 | 8/1996 | |
| WO | WO2015028798 A1 | 3/2015 | |

OTHER PUBLICATIONS

Ash, et al, Clinical Trials of the T-Fluted (Ash Advantage) Peritoneal Dialysis Catheter, Apr. 2002, pp. 133-143, vol. 9, No. 2, Advances in Renal Replacement Therapy, available at doi.org/10.1053/jarr.2002.33526.

Tenckhoff et al, Bacteriologically Safe Peritoneal Access Device, 1968, pp. 181-187, vol. XIV, Trans. American Society of Artificial Internal Organs, available at https://journals.lww.com/asaiojournal/pages/default.aspx.

Google, English machine translation of JPH08206219, Dec. 30, 2020, 4 pages.

* cited by examiner

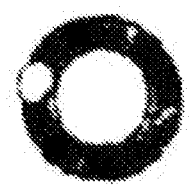
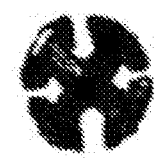
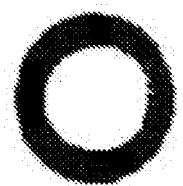
Prior Art
Figure 2

SLOTTED PERITONEAL ACCESS CATHETER

CROSS REFERENCE

This U.S. non-provisional application claims the benefit of U.S. provisional application No. 62/594,079, filed Dec. 15, 2017, the subject matter of which is expressly incorporated by reference herein.

FIELD

Design for PD catheter with slot shaped outflow ports.

BACKGROUND

Peritoneal dialysis (PD) is a successful home dialysis therapy, and much of its success derives from the overall success of the catheters used to access the peritoneum. Chronic peritoneal dialysis (PD) catheters are the most successful of all transcutaneous access devices, with longevity and successful function measured in years rather than days to months. They are constructed of soft materials like silicone rubber. The intraperitoneal portion usually contains 0.5-0.75 mm diameter side holes but one version has linear grooves or slots rather than side-holes (the Advantage™ Catheter by Medigroup, now discontinued). All chronic PD catheters have one or two extraperitoneal Dacron® cuffs, that promote a local inflammatory response. In a unique example of beneficial bio-incompatibility the sclerotic process produces a fibrous plug to fix the catheter in position, prevent fluid leaks, and prevent bacterial migration around the catheter. In spite of general success, peritoneal access failure is still a continued source of frustration for all PD programs. The most common problem of catheters is infection, but outflow failure is the second largest cause of PD catheter failure. Catheter failure is the reason for "dropout" from such programs in at least 25% of patients. Increasing the success of Continuous Ambulatory Peritoneal Dialysis (CAPD) or Continuous Cycler Peritoneal Dialysis (CCPD) program requires optimizing the function of peritoneal catheters.

As shown in prior art FIG. 1, there appears at first to be a wide variety of chronic peritoneal catheters. However, each portion of the catheter has only a few basic design options. There are four designs of the intraperitoneal portion of current catheters: Straight Tenckhoff, with an 8 cm portion containing 0.5-0.75 mm side-holes arranged in four longitudinal rows on the distal half of the catheter; Curled Tenckhoff, with a coiled 16 cm portion also with side-holes as above; Straight Tenckhoff with perpendicular discs (Toronto-Western, rarely used); and T-fluted catheter (Ash Advantage™) with grooved (fluted) limbs positioned against the parietal peritoneum.

There are three basic shapes of the subcutaneous portion between the muscle wall and the skin exit site: Straight, or gently curved; A 150-degree bend or arc (Swan Neck™), and A 90-degree bend, with another 90-degree bend at the peritoneal surface (Cruz® "Pail Handle" catheter).

There are three positions and designs for Dacron® cuffs: Single cuff around the catheter, usually placed in the rectus muscle but sometimes on the outer surface of the rectus; Dual cuffs around the catheter, one in the rectus muscle and the other in subcutaneous tissue; and Disc-ball deep cuff, with parietal peritoneum sewn between the Dacron disc and silicone ball (Toronto Western and Missouri catheters).

There are three internal diameters of PD catheters, each having outer diameter of approximately 5 mm (see prior art FIG. 2): 2.6 mm, the standard Tenckhoff catheter size; 3.1 mm, the Cruz catheter; and 3.5 mm, the Flexneck™ catheter.

There are two materials of construction: silicone rubber (nearly all catheters) and polyurethane (Cruz™ catheter, no longer available).

The various intraperitoneal designs were all created to diminish outflow obstruction due to the normal diminution in flow which occurs as peritoneal surfaces approach the catheter, or due to omental attachment to the catheter. The shape of the curled Tenckhoff catheter and the discs of the Toronto-Western catheter hold visceral peritoneal surfaces away from the side-holes of the catheter to some degree. The grooves of the Advantage™ catheter distribute flow over the surface of the limbs that contact the parietal peritoneum, providing a much larger surface area for drainage than side-holes provide. An irritated omentum attaches firmly to side-holes of a catheter but only weakly to grooves on a catheter (as demonstrated by the Blake™ surgical drain, with grooves on the catheter surface). The Advantage™ catheter provided dialysate outflow rates equal to the most successful Tenckhoff catheters, and better than most such catheters. The internal cross-shaped walls of the Advantage catheter caused the hydraulic resistance of each lumen (or groove) to be high, meaning that fluid entered and left the catheter very near the T-shaped hub, rather than flowing to the ends of the catheter. The longevity of function of the Advantage catheter was greater than that of standard Tenckhoff catheters, due to a lower incidence of outflow failure.

The subcutaneous catheter shapes components of PD catheters all provide a lateral or downward direction of the exit site. A lateral or downward direction minimizes the risk of exit infection. An upward directed exit site collects debris and fluid, increasing the risk of exit site infection.

The optimal location for the standard deep cuff is within or on the outer surface of the rectus muscle. The subcutaneous cuff provides additional protection from bacterial contamination of the subcutaneous tunnel. The disc-ball deep cuff provides security of position of the catheter, since with the peritoneum sewn between the Dacron disc and intraperitoneal ball the catheter is fixed in position and cannot migrate outward. Similarly, the T-shape of the Advantage catheter places the intraperitoneal limbs against the parietal peritoneum (the abdominal lining that is just below the muscle layer), preventing outward migration of the catheter. In the Advantage catheter, the distance between the top of the T-connector and the bottom of the deep Dacron cuff was 7 mm. This positioned the T-connector to rest against the parietal peritoneum while the deep cuff rested against the outer surface of the rectus (abdominal) muscle.

The larger internal diameter of the Cruz and Flexneck catheters provides lower hydraulic resistance and more rapid dialysate flow during the early phase of outflow. In the latter part of outflow, the resistance to flow is determined mostly by the spaces formed by peritoneal surfaces as they approach the catheter. The Advantage catheter provides much larger entry ports for drainage of peritoneal fluid, and clinical studies have demonstrated faster drainage of the peritoneum in early and late phases of outflow, and a decrease in residual peritoneal volume at the end of outflow.

Changing the material of construction of peritoneal catheters has not changed the incidence of complications of the catheters. Polyurethane catheters have no lower incidence of peritonitis or omental attachment leading to outflow failure.

Polyurethane catheters generally have a weaker bond to the Dacron cuff, and loosening of this bond created pericatheter leaks.

There may be advantages in location of the components of chronic peritoneal catheters (see prior art FIG. 3): the intraperitoneal portion may lie next to the parietal peritoneal surface (between the parietal and visceral peritoneum); the coil or deep intraperitoneal portion may be directed towards the pelvis to the right or left of the bladder, behind the inguinal ligaments; the deep cuff may be within the medial or lateral border of the rectus muscle or just outside its sheath; and the subcutaneous cuff may be approximately 2 cm from the skin exit site.

Placing the deep cuff within the rectus muscle or just outside of the rectus sheath promotes tissue ingrowth and therefore avoids peri-catheter hernias, leaks, catheter extrusion, and exit site erosion. At the parietal peritoneal surface, the squamous epithelium reflects along the surface of the catheter to reach the deep cuff. If the deep cuff is positioned very far outside the muscle wall, the peritoneal extension creates a potential or actual peri-catheter hernia. If the deep cuff is resting on the outer rectus sheath and the catheter is fixed in position (such as with the Advantage catheter) then there is no open place for expansion of the reflected peritoneal lining to cause a hernia. Removal of the Advantage catheter becomes somewhat easier because fibrous ingrowth to the cuff is from surrounding subcutaneous tissue rather than from the muscle. After freeing the cuff from fibrous connections and incising the reflected peritoneal surface surrounding the catheter, removal is by simple traction.

At the skin surface, the stratified squamous epithelium follows the surface of the catheter until it reaches the superficial cuff. If the tunnel from subcutaneous cuff to exit site is longer than 2 cm, the squamous epithelium disappears before reaching the cuff and granulation tissue is left, leading to an exit site with continued "weeping" of serous fluid, and the potential for exit site infection is increased. If the subcutaneous cuff is too close to the exit site, then the cuff will irritate the dermis and the exit site will be continually reddened and inflamed.

Some peritoneal catheters have components that provide greater fixation of the deep cuff within the musculature. When the Missouri and Toronto Western catheters are placed, the parietal peritoneum is closed between the ball (inside the peritoneum) and disc (outside the peritoneum). When the T-fluted (Ash Advantage) catheter is placed, the wings open in position adjacent to the parietal peritoneum and perpendicular to the penetrating tube. With these two catheters, outward migration of the catheter is impossible.

The outflow rates of PD catheters are somewhat slow and irregular, and drainage of the peritoneum is never complete. At the start of outflow, the opening of the catheter at the tip always occludes. The rest of the outflow is through the small side-holes. As the abdomen is drained, bowels and omentum (fatty tissue) surround the catheter and decrease the size of spaces for fluid to flow to the catheter. This increases hydraulic resistance and slows the rate of outflow further. Increasing the pressure head during drainage increases the velocity of fluid flow near the catheter and Bernoulli forces, and this draws more tissues near the catheter. For this reason, outflow of PD catheters is performed using a pre-defined negative pressure created by gravity drainage with a 100 cm hydrostatic head (or a mechanical simulation of this constant pressure).

Early in a drainage cycle, for example with a 2 liter intraperitoneal volume, the flow rate may be 300 mL/min or more. However later in outflow the flow rate decreases to 50 mL/min of flow or less, even though 300-500 mL of fluid may remain within the peritoneum at the time. The reason for this diminution of flow is that during outflow of PD fluid the flow is through the tiny side-holes of the PD catheter. This results in a rapid velocity of fluid through each side-hole and this velocity creates a suction (or Bernoulli force) on the omentum and bowel loops near the catheter. As these surfaces draw close to the catheter the space available for fluid flow towards the catheter. Hydraulic resistance increases and the rate of outflow of fluid diminishes.

With current PD catheters patients who perform PD manually find it difficult to determine the optimal time to end the outflow of fluid and begin the inflow of new fluid. When the outflow of fluid becomes slow, it is frustrating to wait 5 or 10 minutes to drain additional intraperitoneal fluid, and there is little dialysis occurring when the peritoneum is nearly dry. On the other hand, the residual peritoneal fluid volume remains within the peritoneum at the start of next inflow, diminishing the volume of fresh fluid that is comfortable to the patient and decreasing overall chemical clearance. For machine automated PD, algorithms have been implemented to determine the functional "end of outflow." For example, one algorithm determines the outflow to be complete when the volume recovered equals 75% of the infused volume AND the outflow rate has diminished to 50 mL/min or less. Due to the variability of outflow rate with current Tenckhoff-type PD catheters outflow alarms are the most frequent and bothersome of automated PD. If the patient bypasses these alarms repeatedly, they can have significant overfilling of the peritoneum during automated PD, causing discomfort and in severe cases difficulty in breathing.

The outflow of fluid through Tenckhoff type catheters can cease altogether in some patients. In this complication fluid can be infused easily but drainage of fluid is nearly zero. This obviously interrupts the dialysis therapy altogether. Usually the cause is attachment of omentum (fatty tissue in the abdomen) to some part of the catheter, which results in a "ball-valve" action of the surrounding omentum, causing the one-way function of the catheter. Outflow failure is the most frequent cause of PD catheter failure, besides infection. Clinical experience with the Advantage catheter indicated that outflow failure was very rare, and direct attachment of omentum to the catheter surface was never found. If omentum penetrated through the slots at any time, it apparently formed a very weak attachment, at most.

PD therapy would be easier to perform, less stressful and time-consuming and more chemically effective if PD catheters drained the peritoneum more quickly, more completely, and more predictably. The best way to accomplish this is to provide larger ports for draining the fluid. However, merely making the side-holes larger than 0.5-0.75 mm has resulted in a greater incidence of outflow failure, since the omental tissue is active, and attaches to the larger holes more easily. In the 1990s Dr. Ash designed and helped to develop the Advantage catheter (described above and shown in FIGS. 1 and 2). This catheter had 1 mm-wide linear slots on the surface rather than side-holes. Internal "criss-cross" walls supported the general cylindrical shape of the catheter and allowed the slots to extend the whole length of the catheter. The overall catheter shape was somewhat similar to the "Blake" or "Jackson-Pratt" surgical drains used for a completely different purpose, draining small amounts of infected fluid from abscesses or body spaces. In clinical trials this catheter demonstrated more complete and consistent drainage of the peritoneum during PD therapy, However, the flow rate during the early phase of outflow was not much higher than with the Tenckhoff catheter and x-ray studies showed that fluid actually left and entered only through the slots nearest the central hub. The criss-cross walls within the catheter made four small channels for fluid flow within the catheter, decreasing the diameter of each channel and increasing the hydraulic resistance to flow down the channels. The catheter was successful but there were production problems, and it was more expensive and difficult to place than standard Tenckhoff catheters. For these reasons, it is no longer marketed.

Effective peritoneal access is needed for other therapies besides PD. The peritoneum is a site for growth and metastasis of a number of types of abdominal cancer. When there is extensive spread of cancer within the peritoneum, this is called "peritoneal carcinomatosis." An effective therapy for peritoneal carcinomatosis is Hyperthermic Intraperitoneal Chemotherapy (HIPEC) in which heat is used to augment the cancer killing effect of anticancer drugs. In HIPEC the patient undergoes general surgery and the abdomen is opened, or inspected with a laparoscope. Cancer is removed from all peritoneal surfaces, and then two large vinyl catheters are placed, each about ¾" in diameter and with numerous large side holes. The incision is then closed around the catheters so that they exit through the abdominal wall. A large bag of saline solution is prepared (about 6 liters). Fluid is removed from the bag and pumped into one catheter at a very high flow rate. Fluid is drained from the other catheter by gravity and returned to the large bag. The fluid is then heated to 42-43 degrees centigrade, and then chemotherapeutic agents are added. The goal is to heat the peritoneum to 41-42 degrees C. and to circulate the heat and chemotherapeutic agent throughout the entire peritoneum to kill cancer cells on all surfaces. To accomplish distribution through the peritoneum, the goal flow rate is 2000 mL/min (5-10 times higher than that which occurs in standard PD therapy). Even with the very large catheters however, the outflow rate does not reach this goal rate and therefore the treatments often are performed with slightly less than the goal flow rate.

At the end of the procedure, the abdomen is opened again, and the catheters are removed. The abdomen is then closed and the patient wakened from anesthesia. The patient is followed carefully to see if there are signs of return of the cancer. If the cancer does return, the same procedure is repeated once, and sometimes repeated every month or so. There would be great advantage to a catheter which provides the same very high flow rates but was soft and flexible and of smaller size, perhaps at most twice the size of the Tenckhoff catheter. Such a catheter could be placed through small incisions in the abdominal wall and could be removed after the HIPEC procedure by mere traction. This would avoid the need for re-opening the abdomen at the end of the procedure. Further, if Dacron cuffs were added to the catheter and suitable external connectors, then the catheters could be left in the abdomen after the first procedure and used for repeated procedures every month or so. HIPEC could then be done as outpatient treatments, since no surgery would be needed for the follow-up treatments.

It would also be helpful to have a chronic catheter in the peritoneal space for infusion of chemotherapeutic agents in treatment of peritoneal cancers. Following operation to remove all visible peritoneal cancer, Early Postoperative Intraperitoneal Chemotherapy (EPIC) is sometimes employed to deliver anticancer drugs directly to the peritoneal space and to contact the remaining cancer. This is performed through a catheter (such as a Tenckhoff) left in the abdomen after surgery. A liter or so of fluid with anticancer drug is infused into the peritoneum and left in place, a few days after surgery. Repeat treatment is desired, such as every three weeks for up to six cycles. However, the catheter often develops adhesions to surrounding tissues or clotting, and does not allow repeated chemotherapy infusions. If the slotted catheter avoided these adhesions and flow failures, it would be ideal for repeated infusions during EPIC.

Finally, any catheter with improved drainage rates in the peritoneum would be valuable in draining naturally occurring fluid in the abdomen such as ascites, and in draining fluid from other body cavities. In all body cavities when fluid is drained through a catheter, the soft tissue surfaces approach the surface of the catheter. The suction forces near small side-holes brings the surfaces close to the holes, causing a "ball valve" blockage of flow. Further, small fluid spaces form around the catheter, increasing hydraulic resistance and diminishing flow rate. Applying excessive negative pressure to the draining fluid can cause the fluid flow to stop altogether. When ascites fluid in the abdomen is drained by gravity, the time spent in draining the fluid may be 15 minutes or more, and there is usually a considerable volume of fluid left in the abdomen after the procedure.

SUMMARY

This patent application describes alternate catheter designs that allow cylindrical PD catheters to have slots on the surface, but without criss-crossing walls inside the cylinders. Thus there is a single large internal lumen of the catheter instead of four small lumens. This greatly diminishes the hydraulic resistance, and results in much higher flow rate through the catheter than any existing peritoneal catheter design.

The present invention includes a unique port design for peritoneal dialysis catheters that allows high outflow and inflow rates, with a minimum fluid velocity through the fluid entry ports. Salient features are: ports which are shaped like long and narrow slots on the surface of circular or oval cylinders catheters with a large central lumen, with material bridges around the slots to maintain the catheter's cylindrical shape and the uniform width of each slot (1 mm or less).

One type of bridge is created by placing slots that are relatively short in a staggered pattern on the surface of a simple cylinder (or oval cylinder). The catheter material between the slots then becomes the bridge to maintain the cylindrical shape. Another type of bridge is a U-shaped "trough' which is created under each slot which spans each slot. Holes in the bottom of each trough pass fluid in and out from the inside of the catheter, but the thin slots prevent omentum and bowel surfaces from touching the holes. This type of bridge allows slots to be long and continuous from one end of the catheter to the other. Either type of catheter can be created by a number of manufacturing processes.

The present invention also includes methods to fix the deep Dacron cuff of the catheter within or next to the abdominal musculature. One approach is a T-shape catheter design with subcutaneous tubing joining to an intraperitoneal portion that is essentially at right angles to the intraperitoneal tubing. Another approach is to create a sharp 150-180 degree bend of the catheter tubing, so that the deep cuff lies in the muscle, one limb is above the abdominal musculature and the other is below the musculature, lying on the parietal peritoneum. This results in a catheter that can be made linear with an internal stylet. Each type of slotted catheter described above can be made in either T-shape or linear.

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein:

FIG. 2. Cross section appearance of current PD catheters. A: Merit Flexneck. B: Cruz (no longer available). C: Standard Tenckhoff. D. Advantage™ or T-fluted (no longer available).

Figure 1:
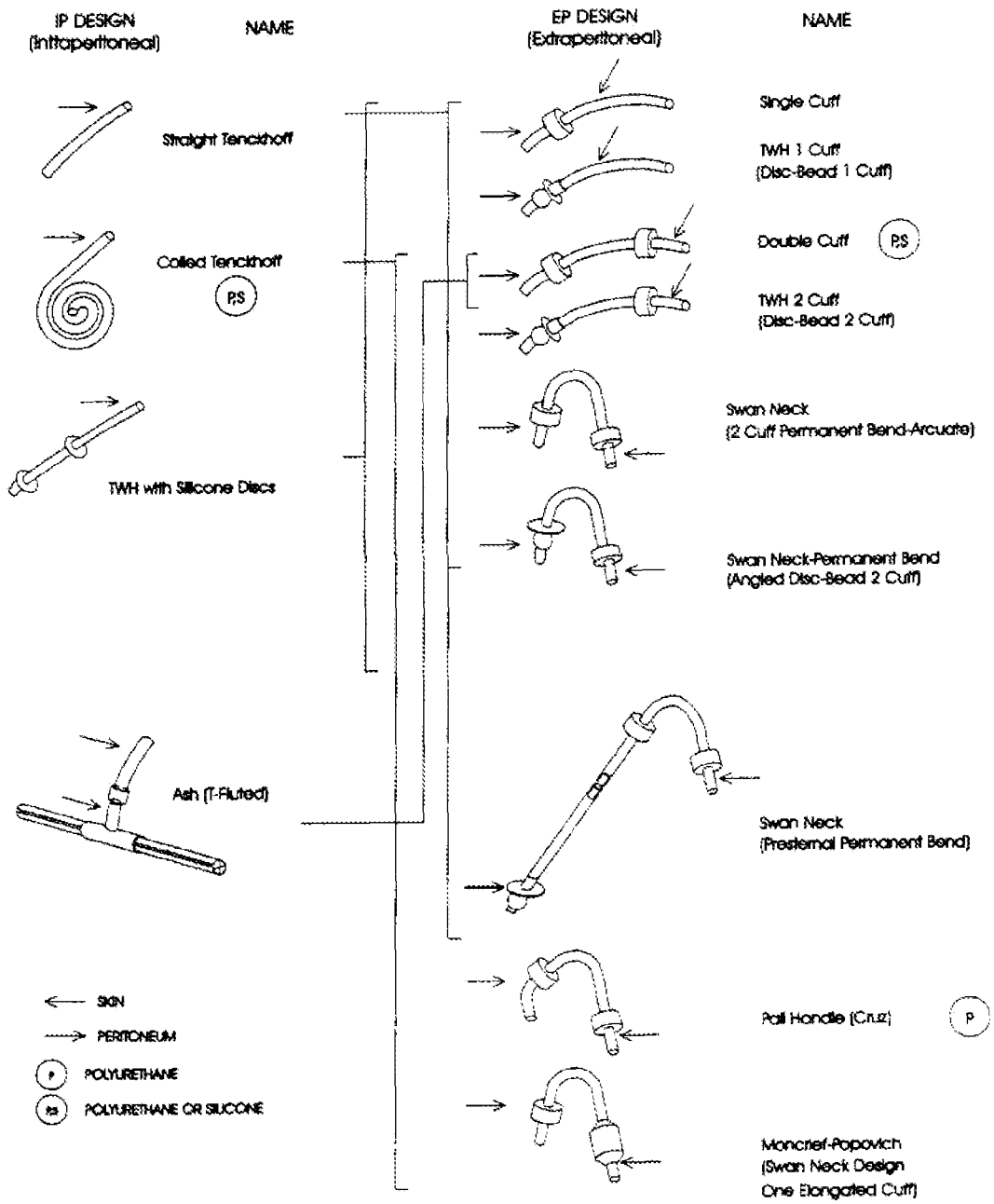
FIG. 1. Current designs of PD catheters. (From Ash S R, Carr D J, Diaz-Buxo J A. Peritoneal access devices: hydraulic function and biocompatibility. In: Nissenson, A R, Fine, R N, and Gentile, D E (eds.) *Clinical Dialysis*. Norwalk, Conn.: Appleton & Lange, 1995, pp. 295-321).
Figure 3:
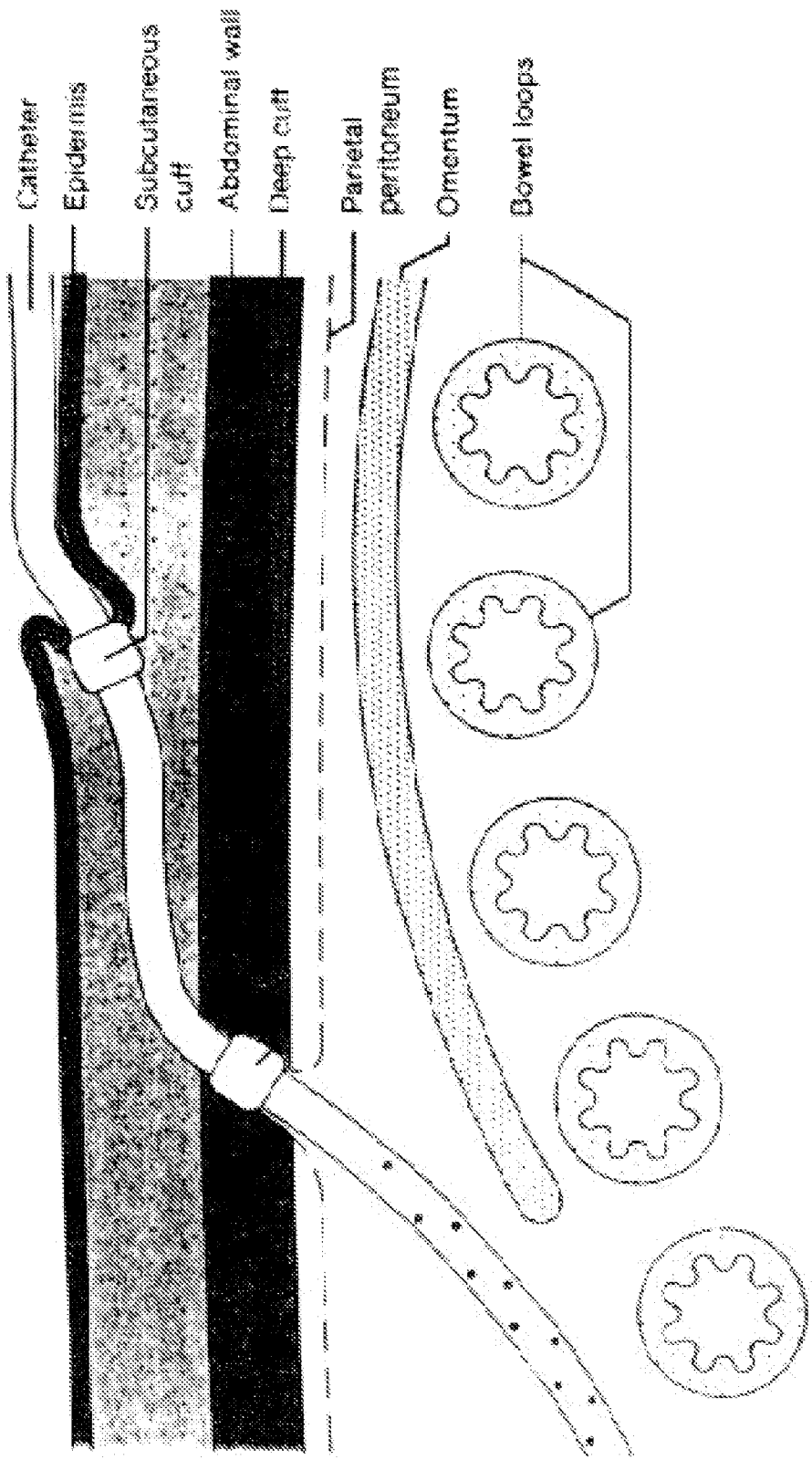
FIG. 3: components of a straight Tenckhoff catheter and relation to body tissues.

Corresponding reference characters indicate corresponding parts throughout the several views. Although the drawings represent embodiments of the present disclosure, the drawings are not necessarily to scale and certain features may be exaggerated in order to better illustrate and explain the present disclosure.

DETAILED DESCRIPTION OF THE EXEMPLARY EMBODIMENTS

The embodiments disclosed below are not intended to be exhaustive or limit the disclosure to the precise forms disclosed in the following detailed description. Rather, the embodiments are chosen and described so that others skilled in the art may utilize their teachings.

We have designed a peritoneal catheter that should allow much more rapid fluid flow into and out of the peritoneum, a fixed position of components relative to the abdominal musculature, and a lower incidence of outflow failure. The key advance is the use of slots for passage of fluid from the peritoneal space to the internal lumen of the catheter.

Figure 4:
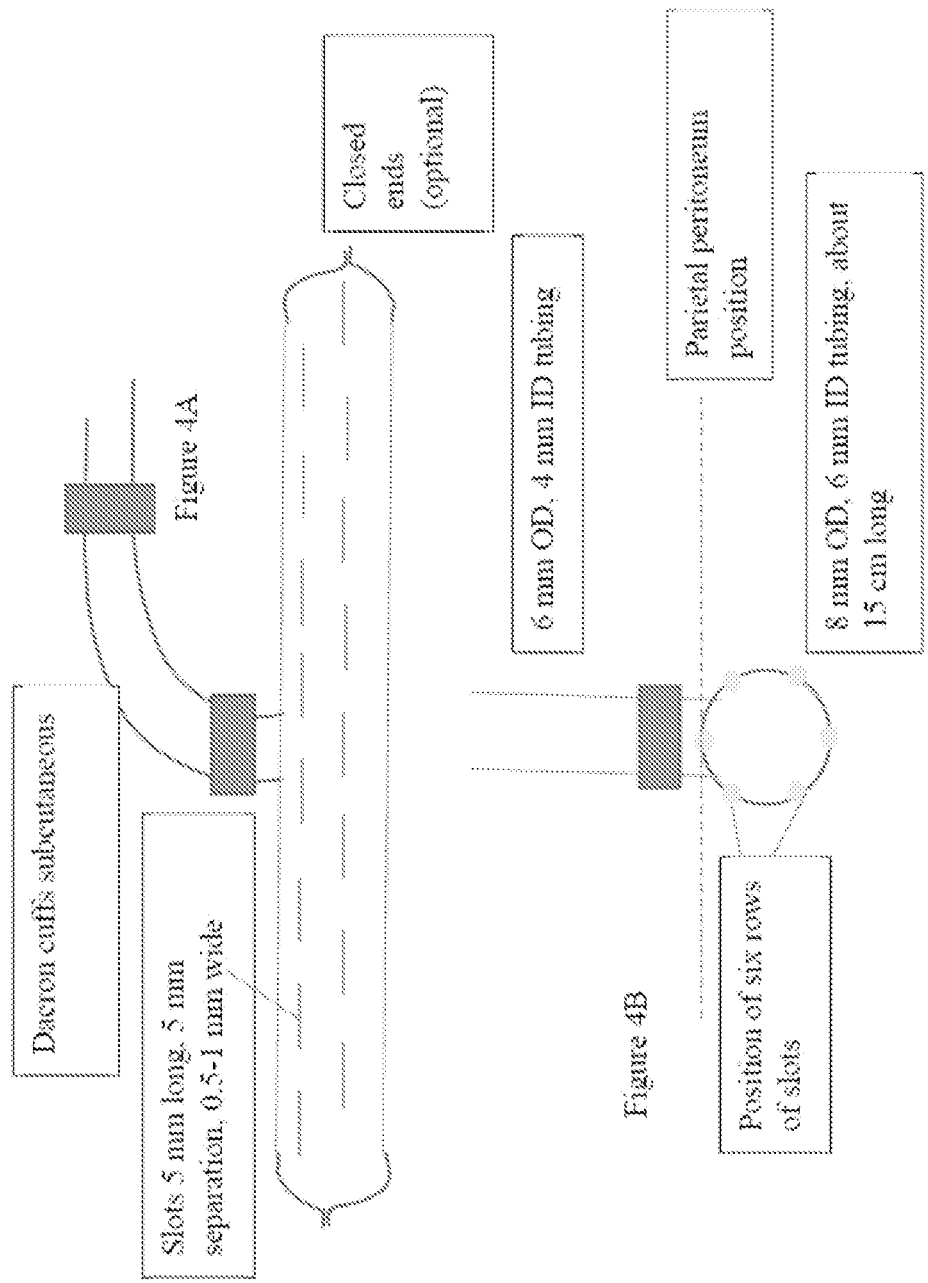
FIG. 4A: a front cross sectional drawing of slotted catheter a staggered-slot catheter in which the slots exist as gaps in a cylindrical body. The slots are discontinuous and staggered in position around the catheter. A single central lumen exists in the slotted portion. In this figure, exit tubing is attached to the middle of the slotted portion, creating a T-shaped catheter that fixes the deep cuff in or near the abdominal musculature and the slotted portion against the parietal peritoneum.
FIG. 4B: a side cross sectional drawing of the staggered-slot slotted catheter of FIG. 4A.
Figure 5:
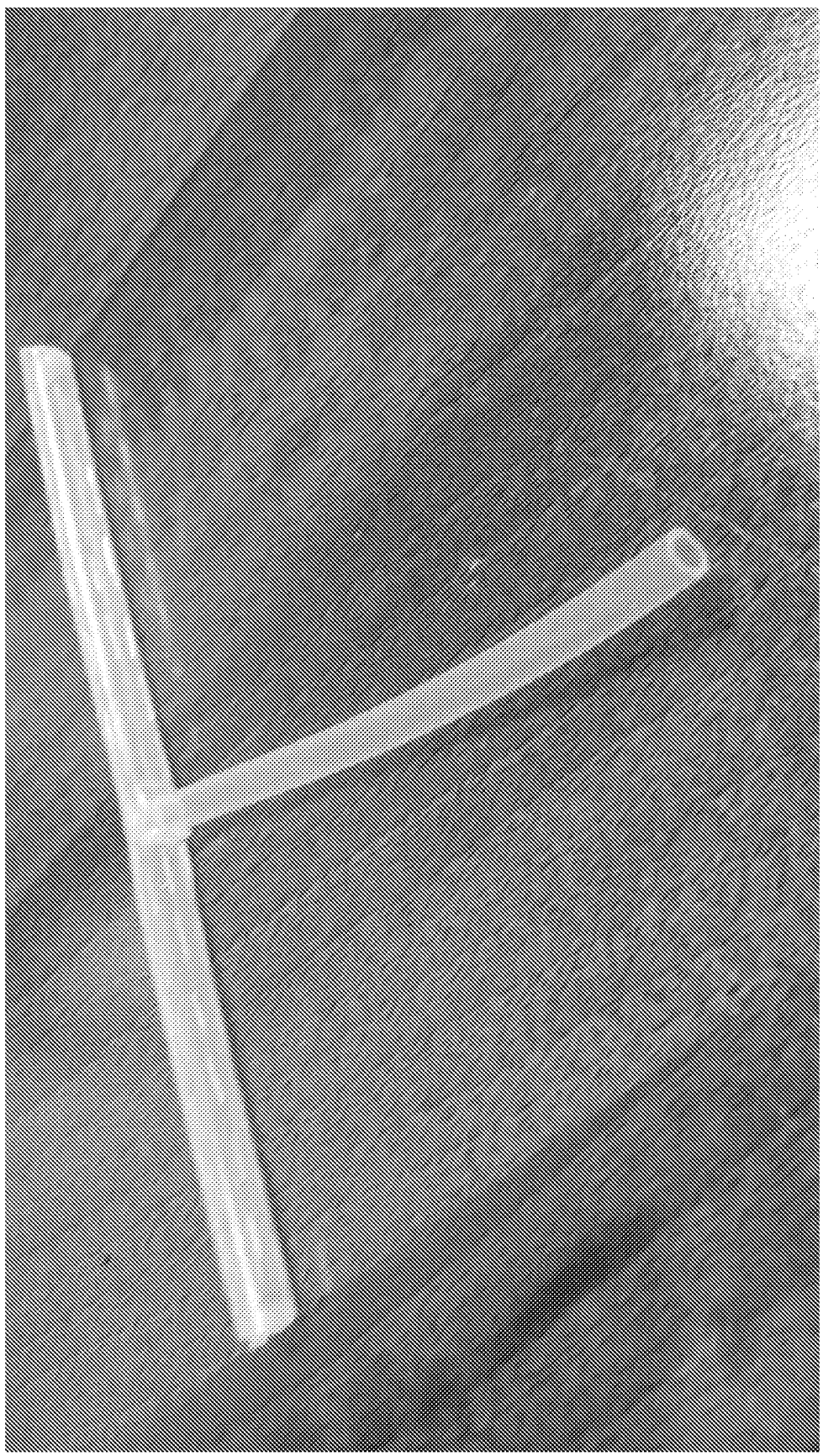
FIG. 5: Photograph of the slotted catheter, a staggered-slot catheter prototype without Dacron cuffs, in the T-shape form.

The slotted catheter will initially be constructed from silicone tubing, although later versions may be in various copolymers. The current staggered-slot design is shown in FIGS. 4A and B and a photograph provided in FIG. 5. It is shown in the T-shaped configuration, with the exit tubing connected to the middle of the slotted portion. The components are: intraperitoneal (IP) portion-8 mm OD and 6 mm ID tubing of 50 durometer, 13-15 cm long; linear slots 0.5-1 mm wide and 5 mm long, spaced 5 mm apart, arranged in six longitudinal lines spaced at 60 degree intervals around the IP portion and with each row of slots "staggered" versus the next row; Closed ends of the IP portion, by one of two methods: flattening the tubing and gluing the sides together, or fitting a molded silicone hemispherical piece to each end; Exit (subcutaneous, or SQ) tubing-6 mm OD and 4 mm ID tubing of 50 durometer, about 12 cm long; Connection of the SQ and IP tubings (end to side) by one of two methods: creating overlapping portions of the two tubings and gluing them together, or over-molding a 0.5-1 mm thick layer of silicone over the junction; Dacron cuffs glued to the SQ tubing, 1 cm long, one beginning 0.7 cm distal the top of the IP tubing and the other 5 cm distal to the first; and Connector on the SQ tubing to fit into ⅜" PVC tubing for drainage and infusion of fluid during HIPEC procedures. We also envision that the IP tubing can be injection molded in a circle or a loop. Slots may be defined in the mold or cut into the IP tubing after injection molding.

Figure 6:
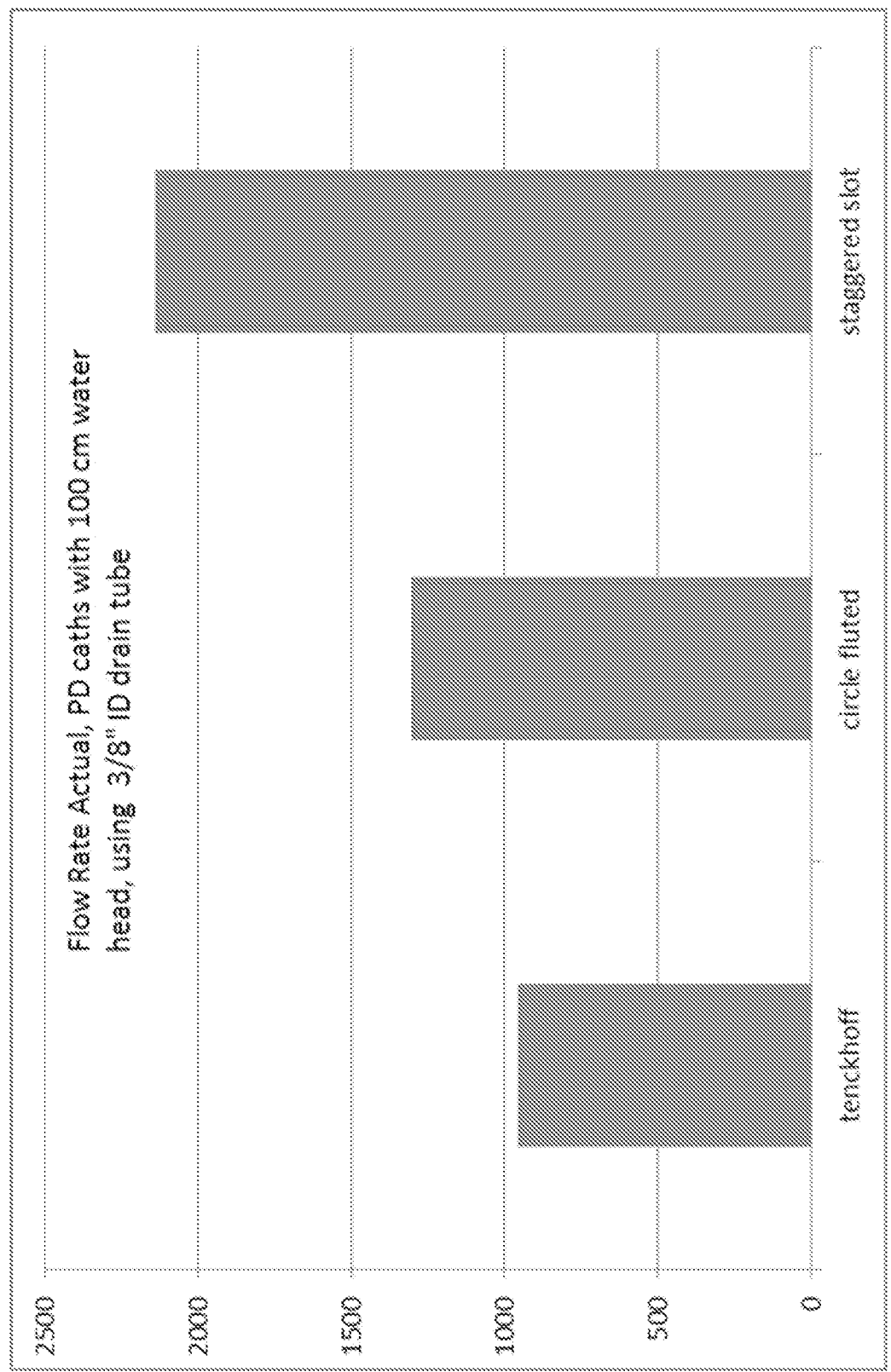
FIG. 6: In vitro data on water flow rate through the staggered-slot catheter, in comparison to the standard Tenckhoff catheter and a catheter containing two 6 mm diameter fluted portions (similar to the Advantage catheter, but larger). Flow rate was by gravity with a 100 cm hydrostatic head through a ⅜" drain tube. The desired flow rate for HIPEC procedures is 2000 mL/min, and this flow was obtained with the slotted catheter.
Figure 7:
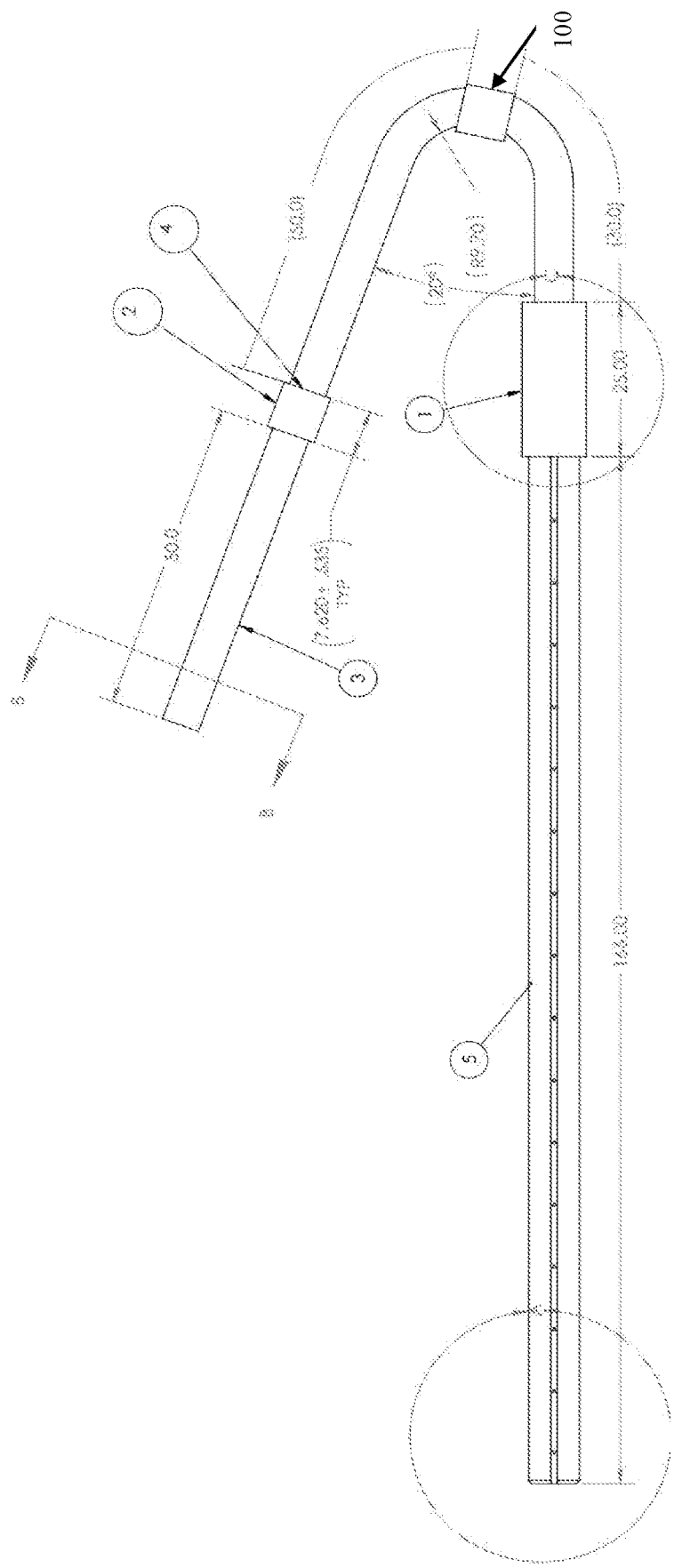
FIG. 7: Drawing of a continuous slot catheter, note Details A, B, & C.
Figure 8:
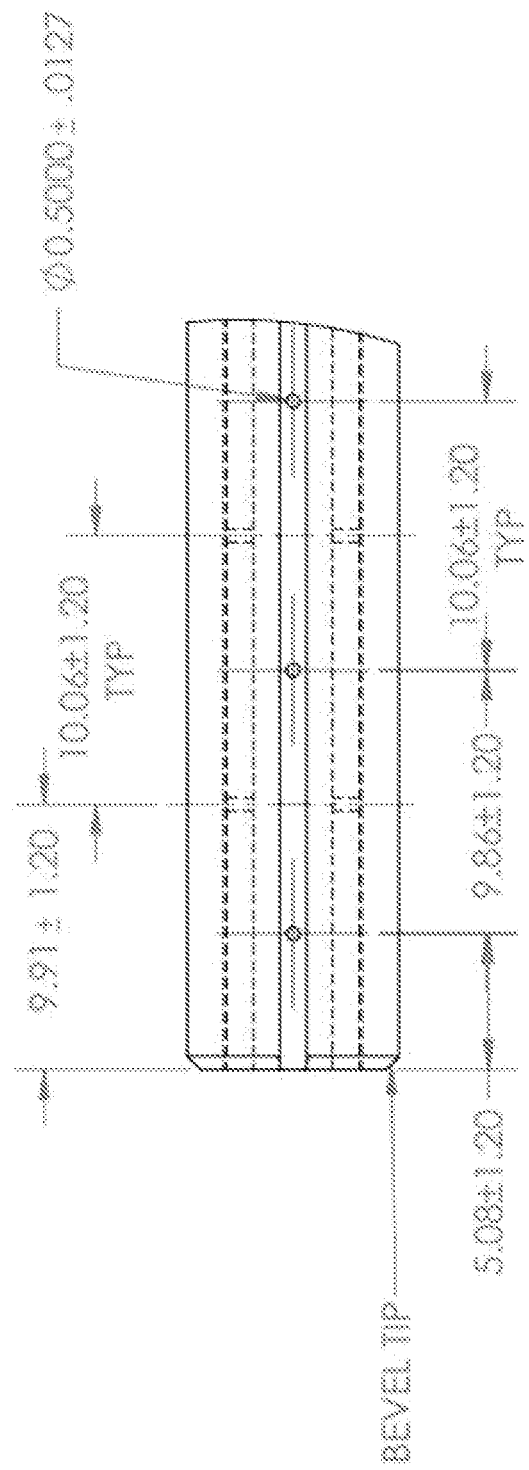
FIG. 8: Drawing of the horizontal cross section of the exit portion (Detail A) of a continuous-slot catheter.
Figures 9A, 9B:
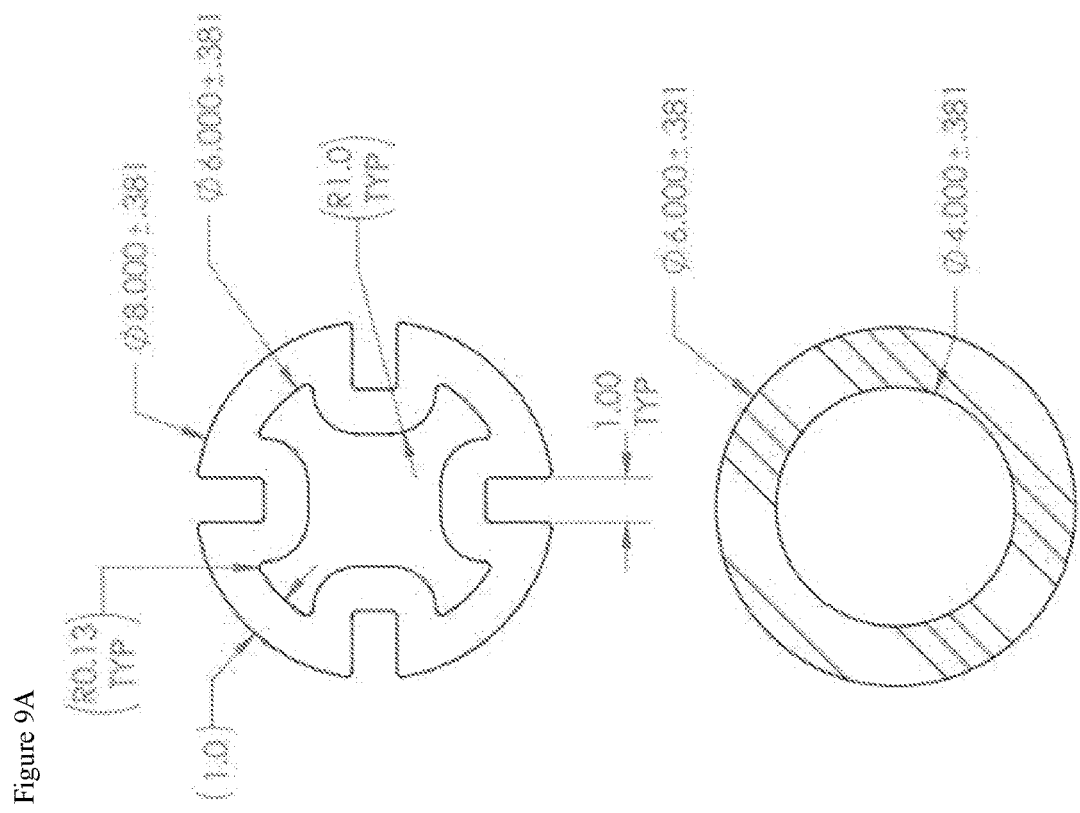
FIG. 9A: Drawings of the vertical cross sections of the exit portion (Detail A) of a continuous-slot catheter.
FIG. 9B: Drawings of the vertical cross sections of the entrance portion (Detail B) of a continuous-slot catheter.
Figure 10:
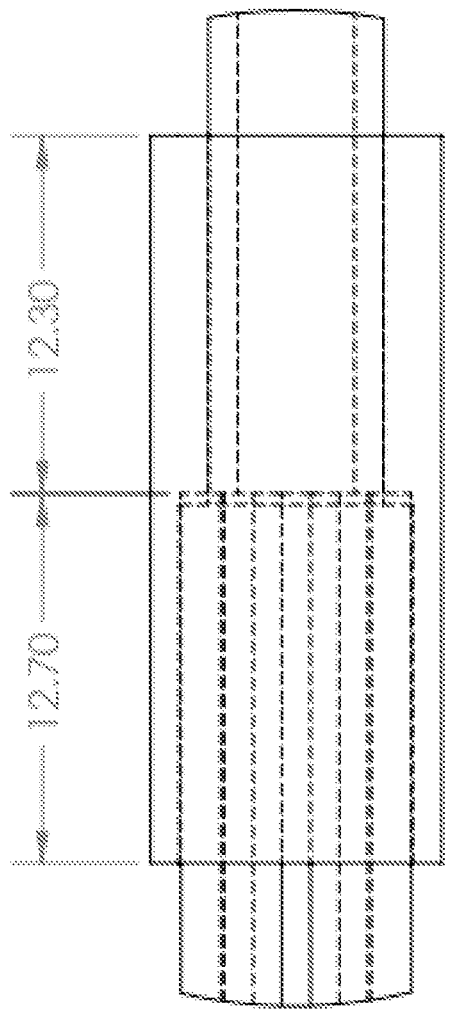
FIG. 10: Drawing of the horizontal cross section of the overmold (Detail C) of a continuous-slot catheter.

The design of the slotted catheter has many features that make in suitable for use in high flow rate CFPD or HIPEC, but also will allow much faster in-out exchanges during peritoneal dialysis. A primary need in HIPEC is a high flow rate of fluid through the peritoneum, preferably over 2000 mL/min. As shown in FIG. 6, during in vitro tests using gravity drainage, the staggered-slot catheter provided flow rate at over 2 liters per minute at 100 cm hydrostatic head. This is about twice as much as the flow through a standard Tenckhoff and an enlarged version of the Advantage catheter (circle fluted). The reason for the high flow rate is the large diameter of the IP portion (6 mm) and the SQ portion (4 mm). Also, the numerous slits of 0.5-1 mm diameter add up to a very large area for fluid transfer. In fact this area is so large that it presents virtually no resistance to fluid flow at all. The flow rate for the slotted catheter is exactly the same in flow test results whether the IP portion is attached or not. The very large area of the slits means that the linear velocity of fluid flow remains very low, even when the overall flow rate is high. This means the catheter will have less tendency to pull omentum or other peritoneal contents towards it at high outflow rate. The slot-shaped ports should avoid omental attachment in a manner similar to the grooves of the Advantage catheter, and for the same reason, there is a high ratio of open area to circumferential area (edges to which the omentum can attach) but there is also a small width of the slot (preventing the ingress of large abdominal contents or their protrusions). The result should be a catheter that avoids outflow failure and allows high flow rates into and out of the peritoneum during all types of peritoneal dialysis procedures, including CAPD, automated PD, CFPD and HIPEC.

In one embodiment, each slot in the continuous-slot catheter is bridged by a U-shaped trough beneath the slot. The bridges support the catheter's cylindrical surface. Circular holes pass fluid into and out of each bridge, at some distance from the surface of the catheter. Exit tubing is attached to one end of this catheter, creating a catheter that can be made linear with an internal stylet. The sharp bend of the catheter holds the deep cuff on or near the abdominal musculature and the slotted portion near the parietal peritoneum.

FIGS. 7-10 include several drawings of the current version of the continuous-slot catheter design. It is shown in the linear catheter design, with the exit (SQ) tubing attached to one end of the slotted portion. The components are an extruded cylindrical tubing of 8 mm OD, 6 mm ID (at maximum), with 1 mm diameter grooves on its surface. Under each groove is a U-shaped "trough" that connects with the outer walls of the cylinder, to support the cylinder walls and the slots. The trough depth is 1 mm. At 1 cm intervals there are 0.5 mm holes drilled into the bottom of each trough. The catheter is shown in the "linear" design, with the SQ tubing fastened to the slotted portion with an overmold. The SQ tubing has a 150 degree bend at the location which passes through the abdominal musculature. This is the position of the deep cuff 100, within or just outside the abdominal musculature. The slotted portion lies just below the parietal peritoneum and the outer SQ portion lies just above the abdominal musculature. These locations tend to fix the deep cuff 100 in position.

For standard PD therapy, one slotted catheter would be placed, allowing input and output of peritoneal dialysis fluid through one catheter. The HIPEC procedure utilizes continuous flow of dialysate through two catheter locations, similar to Continuous Flow Peritoneal Dialysis (CFPD). In HIPEC two of these catheters would be placed during the laparotomy of the HIPEC procedure, at opposite ends of the peritoneal space. One may be placed over the place of origin of the cancer (if known) and the other one at a distant location in the peritoneum. To attain the desired outflow rate using gravity alone, two catheters could be placed for drainage of the abdomen, with a parallel connection to the draining tubing. The catheters could be placed 'inside out" with the SQ tubing being drawn through an opening in the rectus muscle and the IP portion then coming to lie against the parietal peritoneum. They would be used for peritoneal perfusion during the HIPEC procedure, with gravity drainage through a ⅜" diameter PVC tubing into a drainage reservoir 100 cm below the patient. Flow rate would be 2 liters per minute. At the end of the procedure the catheters would be filled with saline and capped. On a weekly basis, they would be flushed with saline. Repeat HIPEC procedures could be done at one month and monthly for up to 6 months. Removal of the slotted catheter will be by dissection to the rectus muscle of the abdominal wall, freeing the deep cuff from surrounding tissue, enlarging the defect in the rectus muscle, and pulling on the SQ tubing to collapse and remove the IP portion.

The slot-shaped ports of the slotted catheter are described here for a T-shaped catheter with a SQ portion attaching to a perpendicular IP portion. However, the function of virtually all existing tubular peritoneal dialysis catheters would be improved by using ports that are not cylindrical but rather oblong or slit-shaped. A single 5 mm slit provides area for flow that far exceeds that of 5 circular holes of similar width. More surface area for flow means lower velocity of PD fluid at any given outflow or inflow rate.

Besides high outflow rate with low velocity at the entry slots, the slotted catheter has other advantages as a chronic catheter: Fixed position with the IP portion against the parietal peritoneum, avoiding possibility for extrusion of the catheter or its cuffs, and avoiding migration of the IP portion within the peritoneum; The large diameter of the IP portion, which naturally tends to hold abdominal contents away from the slits; and Position of slits completely around the IP portion, assuring that most will avoid contact with the parietal peritoneum or abdominal contents.

Example: Comparison of Outflow Properties

The Tenckhoff catheter (Maxflow) was evaluated against the Grooved catheter extruded section, with 1 and 3 holes/cm by S. R. Ash and D. J. Carr of HemoCleanse Technologies LLC.

A frustrating feature of Tenckhoff catheters is that they drain the abdomen slowly and as the intraperitoneal volume decreases, there is a decrease in outflow rate. This demonstrates that there is an increasing hydraulic resistance to flow through the tissues around the catheter. With a continually decreasing flow rate, it is impossible to tell how much fluid remains to be drained from the peritoneum, and in fact the space is never completely drained. Often 300-800 ml of dialysate fluid remains in the abdomen at the end of outflow, whether the outflow is directed by manual exchanges or by cycler machines. Further making peritoneal dialysis difficult, the outflow drainage of the catheters varies cycle by cycle.

Also, as the volume of the peritoneum becomes less, there is less space for fluid flow between surfaces of adjacent abdominal structures, as shown in the adjacent drawing. Peritoneal surfaces will almost always occlude the lumen at the tip of the catheter during outflow. The holes of Tenckhoff catheters should not be much larger than 0.5 mm diameter, to avoid attachment of omentum directly to the holes. This results in very small area of each hole and subsequently a quite high velocity of fluid through each hole (5 cm/sec at only 100 ml/min) The reason that a slotted catheter will work better when near to peritoneal surfaces is that its total area for fluid flow is much greater than that of the small Tenckhoff holes, for example 400 $mm^2$ versus only 32 $mm^2$. This means that velocity into the grooves (if distributed evenly) would be 0.4 cm/sec at 100 ml/min overall flow. The ratio of velocities for entry of fluid to the Tenckhoff catheter and the slotted catheter is thus 12:1. Since Bernoulli (suction) forces are proportional to the square of velocity, the Tenckhoff catheter would create 144 times as much suction force on surrounding tissues as the slotted catheter. Of course the catheter with continuous slots also has 0.5 mm holes, but these are in the bottom of each slot (or, groove), and should therefore be protected from coming next to peritoneal surfaces. Further, there will be many more 0.5 mm holes than in a Tenckhoff catheter. The prototypes tested below have 1 hole per cm, or 40 in a 10 cm section (with 4 grooves). It is envisioned that other prototypes will have 3 holes per cm, or 30 per 10 cm groove, making 120 in a 10 cm section. The increase in number of holes will diminish hydraulic resistance further. Also, linear velocity will be diminished at the holes, which means that flow should be more uniform along the length of the grooves.

Figure 11:
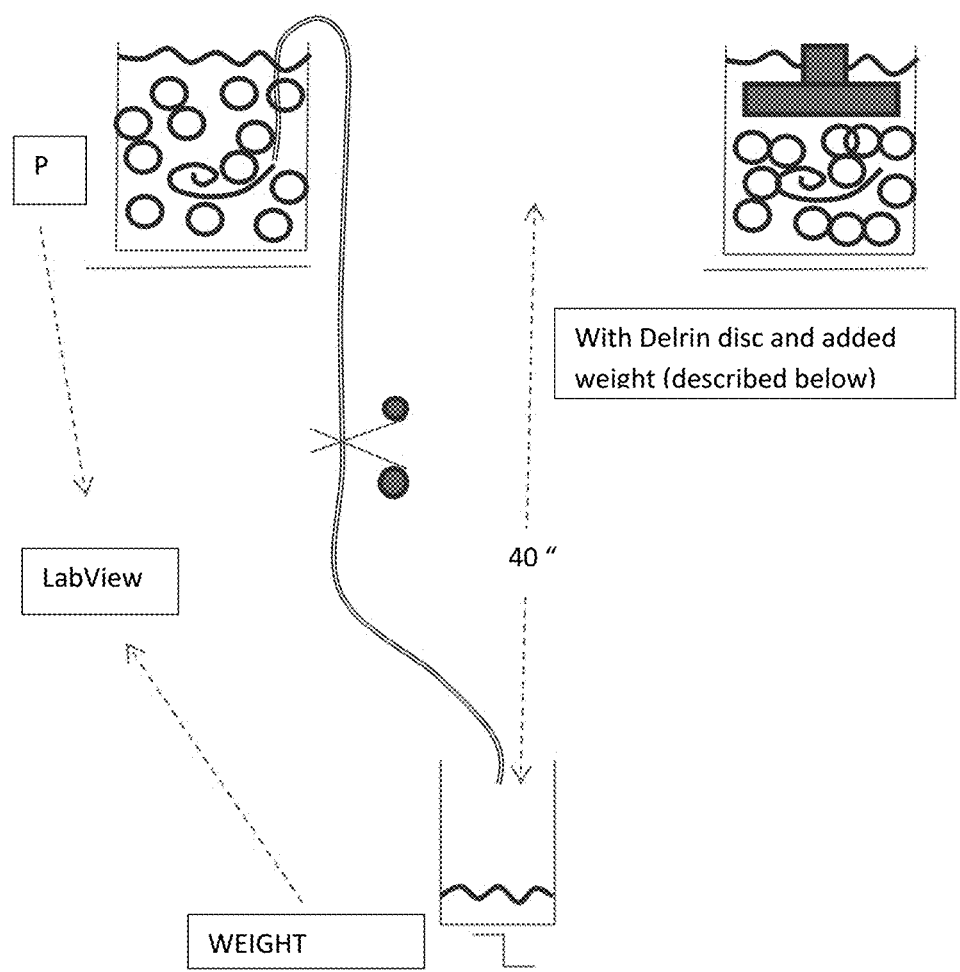
FIG. 11: Drawing of an in vitro model developed to replicate the mechanical properties of the bowel and omental surfaces, and to simulate the way these surfaces surround the catheter during outflow of fluid.

Some years ago we developed in vitro model to replicate the mechanical properties of the bowel and omental surfaces, and to simulate the way these surfaces surround a peritoneal catheter during outflow of fluid. We found that cellulosic dialysis tubing worked very well as an exceedingly soft and pliable material which came in cylindrical shape, with a diameter of 1". This tubing was cut to lengths of 6-12 inches, and one end was tied off. Water was added to the tubing until it was filled about 50%, and then the other end was tied off. Enough of these tubings were made so that they filled 3 liters of a 5 liter container, when all lying together. A shortened peritoneal catheter was placed between layers of the tubings, at the level of about 1 liter fill of the container. The catheter was connected to a ¼" vinyl tube using a large bore connector. The vinyl tube was placed over the lip of the container, and the distal end extended downward to a point 40" below the level of the catheter. A container below the tip of the catheter collected effluent and the container was weighed on a scale. Pressure was measured at the level of the catheter. Weight, time and pressure data was transferred in real time to a LabView data collection system. About 1.5 liters of water was then added to the top of the container, and the vinyl tubing was primed with water. Outflow was begun by unclamping the vinyl tubing. The gravity pressure head thus simulated that used in peritoneal dialysis. A drawing of the experimental setup as tested is shown in FIG. 11.

Figure 12:
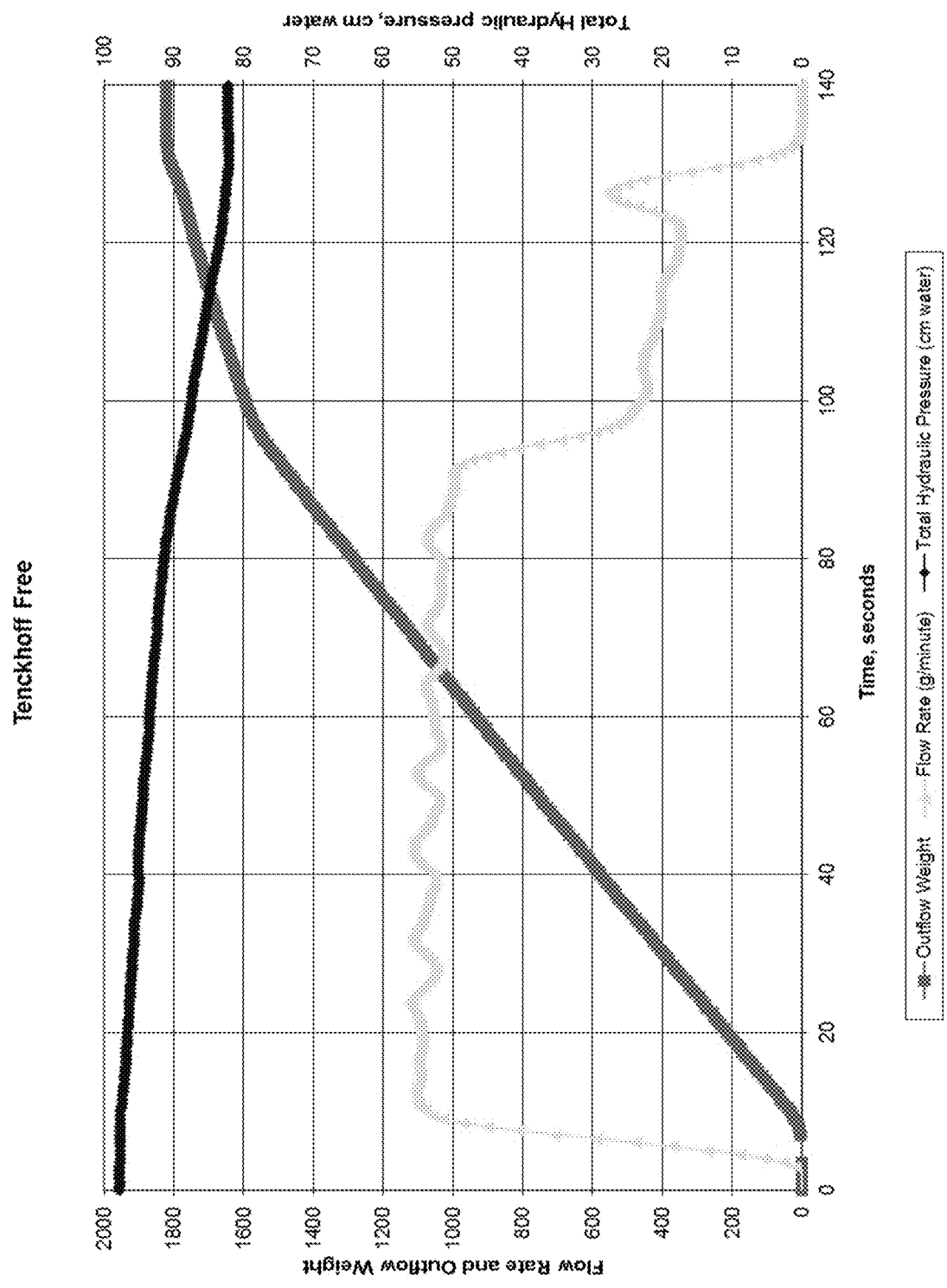
FIG. 12: Chart of Tenckhoff free flow rate and total hydraulic pressure and outflow weight against time (with no bowel compression).
Figure 13:
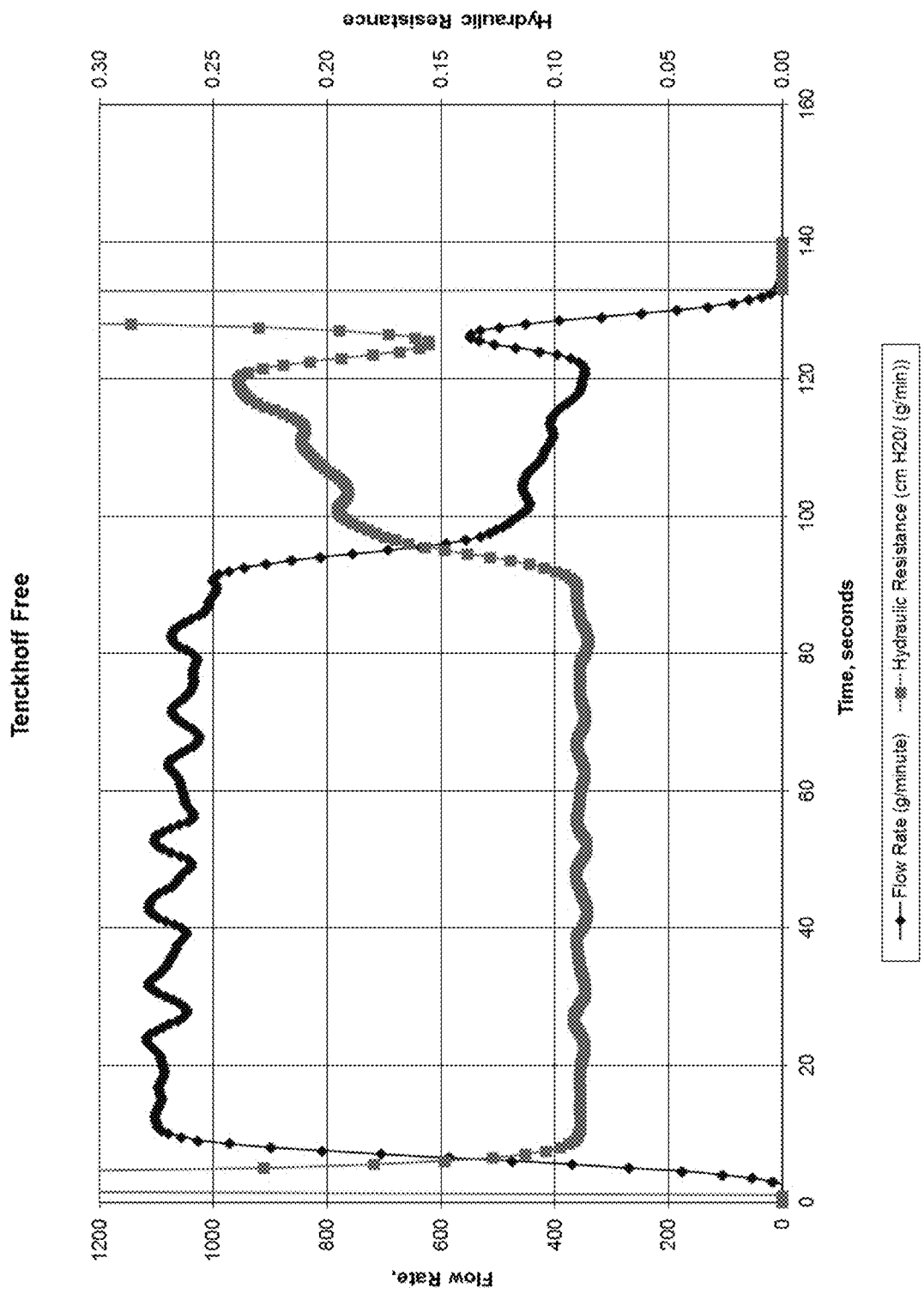
FIG. 13: Chart of Tenckhoff free flow rate and hydraulic resistance against time.

It was noted that on addition of the extra fluid to the container the cellulose tubings tended to separate and some floated to the top of the fluid level. The spacing between the cellulose tubes was greater than would occur between bowel loops and omentum during peritoneal dialysis, even with very large fill volumes (less than 1 mm space, on average). In the first test there was no effort made to hold the bowel loops next to the catheter. This test was performed using a standard Tenckhoff catheter. The coiled MaxFlow catheter was chosen because it has a larger diameter than any of the other Tenckhoff catheters (3.5 mm vs 2.5 mm ID). FIG. 12 shows the outflow fluid weight (volume in ml), the outflow rate in grams (ml) per minute, and the overall hydrostatic pressure head. The X axis is time of outflow, in seconds. When the air-fluid interface reached the catheter, the vinyl tubing filled with air and flow stopped. FIG. 13 shows the same curve for catheter flow rate, and also the calculated hydraulic resistance of the whole drainage system.

Figure 14:
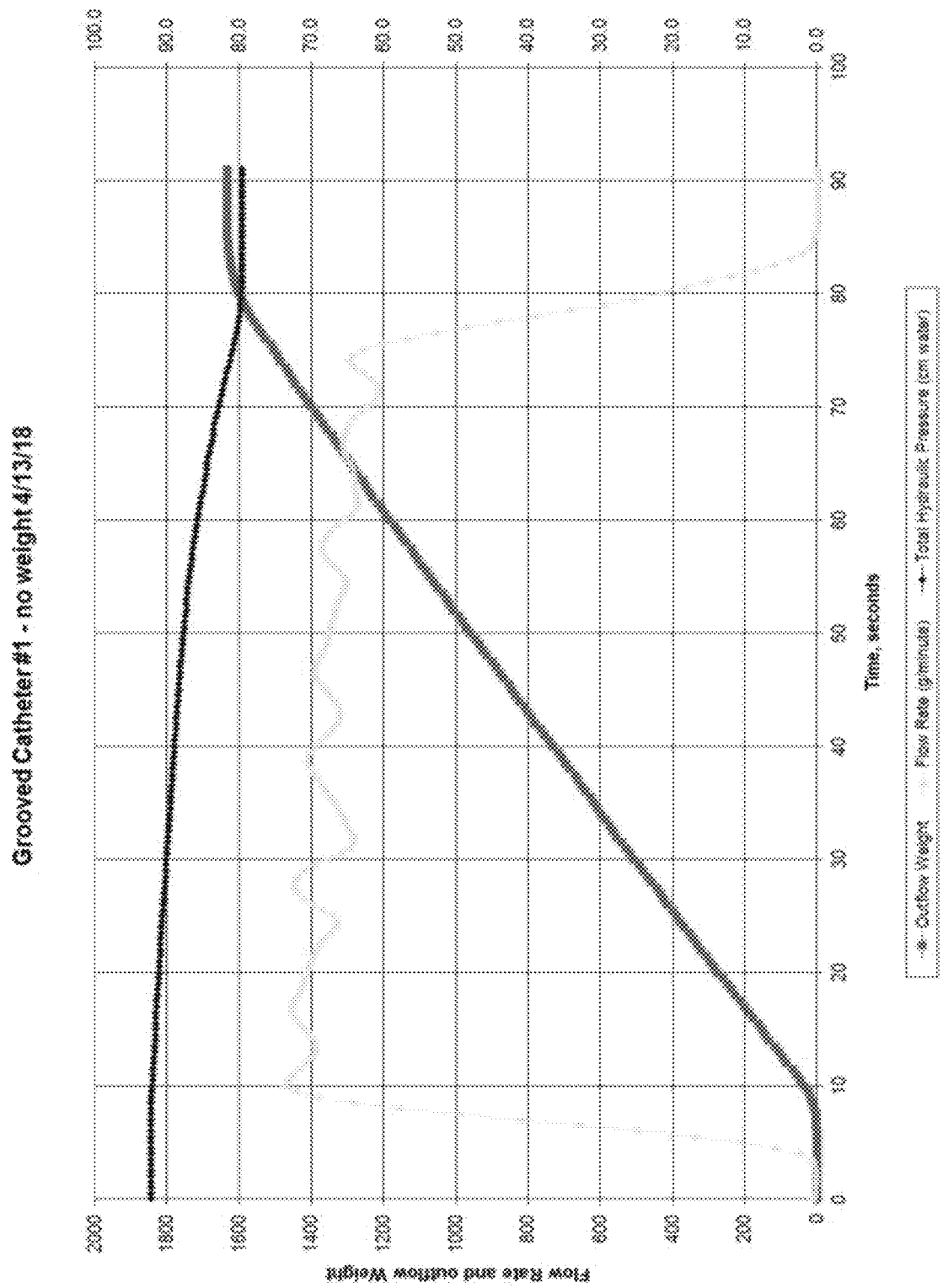
FIG. 14: Chart of Grooved catheters of the present embodiment, flow rate and total hydraulic pressure and outflow weight against time (with no bowel compression).
Figure 15:
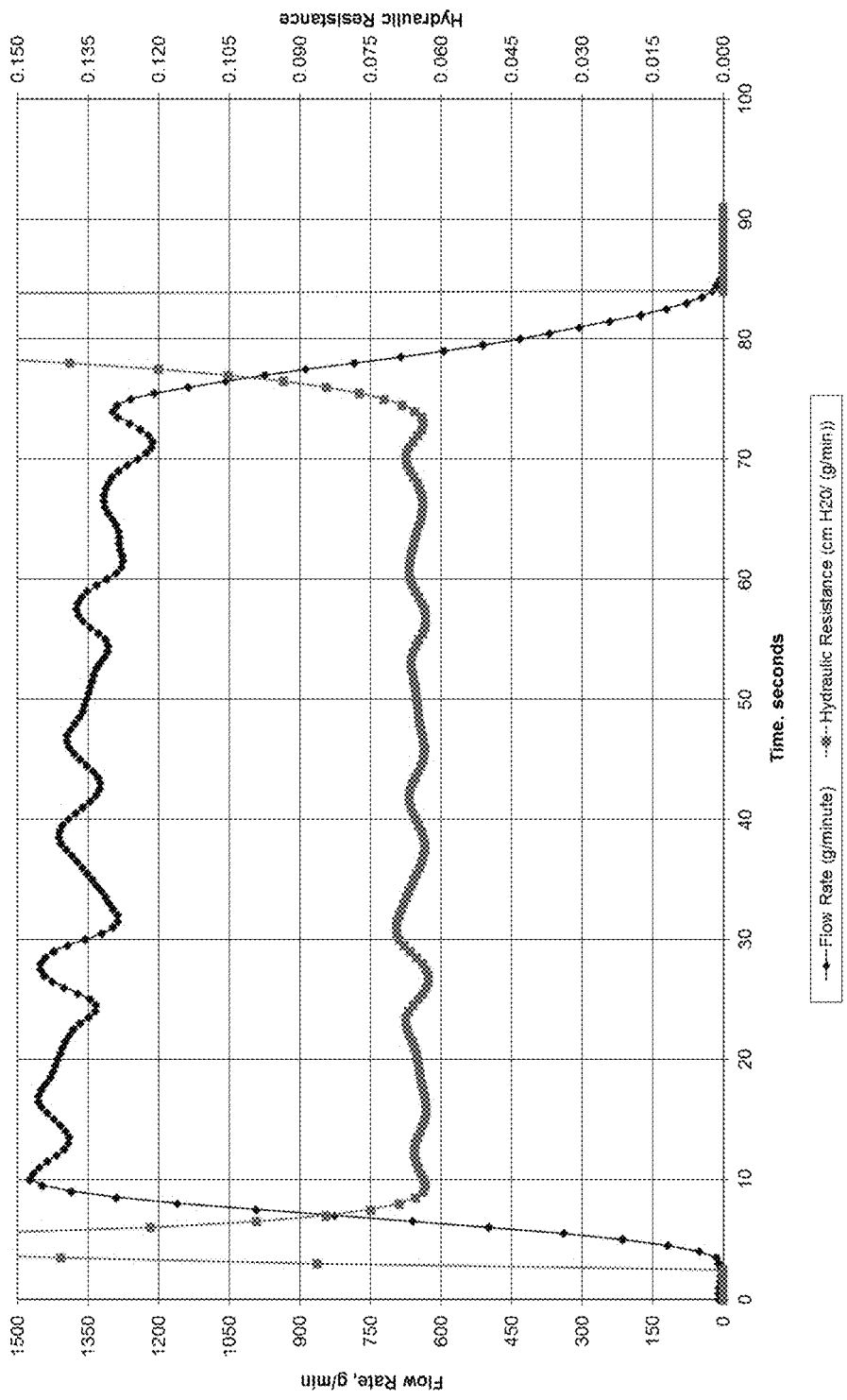
FIG. 15: Chart of Grooved catheters of the present embodiment, flow rate and hydraulic resistance against time.

The next experiments were with the Grooved catheter, containing one hole per cm length of each groove (48 holes altogether). The section was 16 cm long. The distal end was open. The catheter section was attached to the same large bore connector and ¼" ID vinyl tubing as the Tenckhoff catheter, described above. In the first experiment with the Grooved catheter, the cellulose tubings were not restrained in position. As illustrated in FIGS. 14 and 15, outflow of the catheter was higher than with the Tenckhoff catheter (about 1400 ml/min vs. 1000 ml/min). More importantly, the outflow rate didn't change as the air-fluid level went down and cellulose tubings were exposed above the fluid. At about 80 seconds, the air-fluid level reached the catheter and outflow of fluid stopped.

Figure 18:
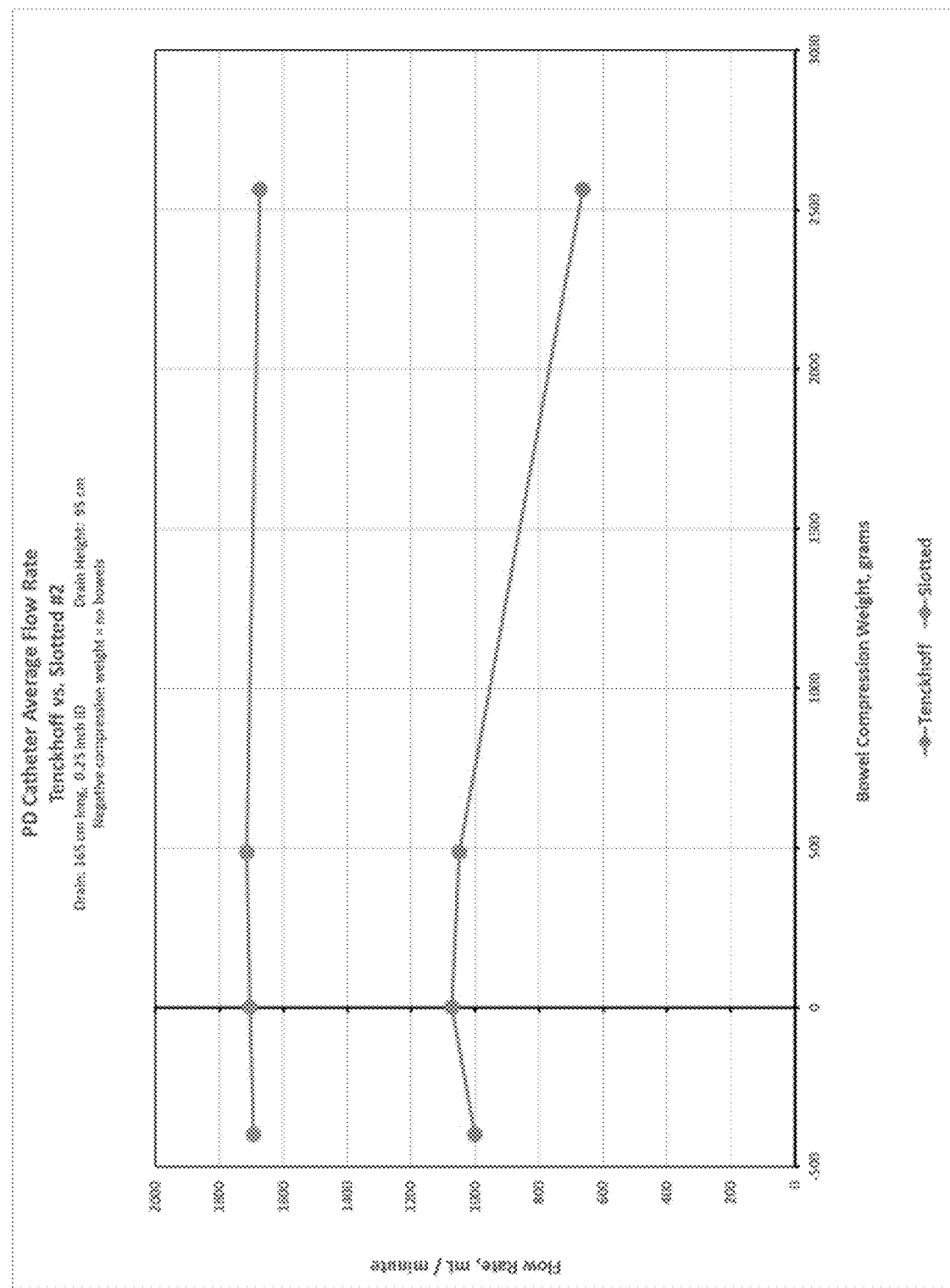
FIG. 18: Chart comparing results for Tenckhoff Free and Slotted catheters of the present embodiment, flow rate versus weight causing bowel compression.

In the next experiment, the Delrin disc (weighing about 500 grams) was placed on top of the pile of cellulose tubings, and fluid was added around and above the disc. As opposed to the Tenckhoff catheter, outflow rate was not diminished, and there was no deceleration of flow as the air-fluid level progressed downward through the container (exposing some of the cellulose tubings). Outflow of fluid continued until the air-fluid level reached the catheter segment and air entered the vinyl drain tube. Hydraulic resistance was essentially unchanged throughout the drainage cycle, as shown in FIG. 18.

The final experiment was done with addition of a 2 kg weight to the top of the Delrin disc. As in the previous experiments, outflow was unimpeded, and remained at 1200-1300 ml/min until the fluid above the catheter was completely drained. There was no deceleration of flow rate as the fluid level declined. Although 2 kg seems like a large amount of weight, with its distribution over the Delrin disc it resulted in pressure of approximately 10 cm $H_2O$, which is similar to the normal human intraperitoneal pressure.

Figure 16:
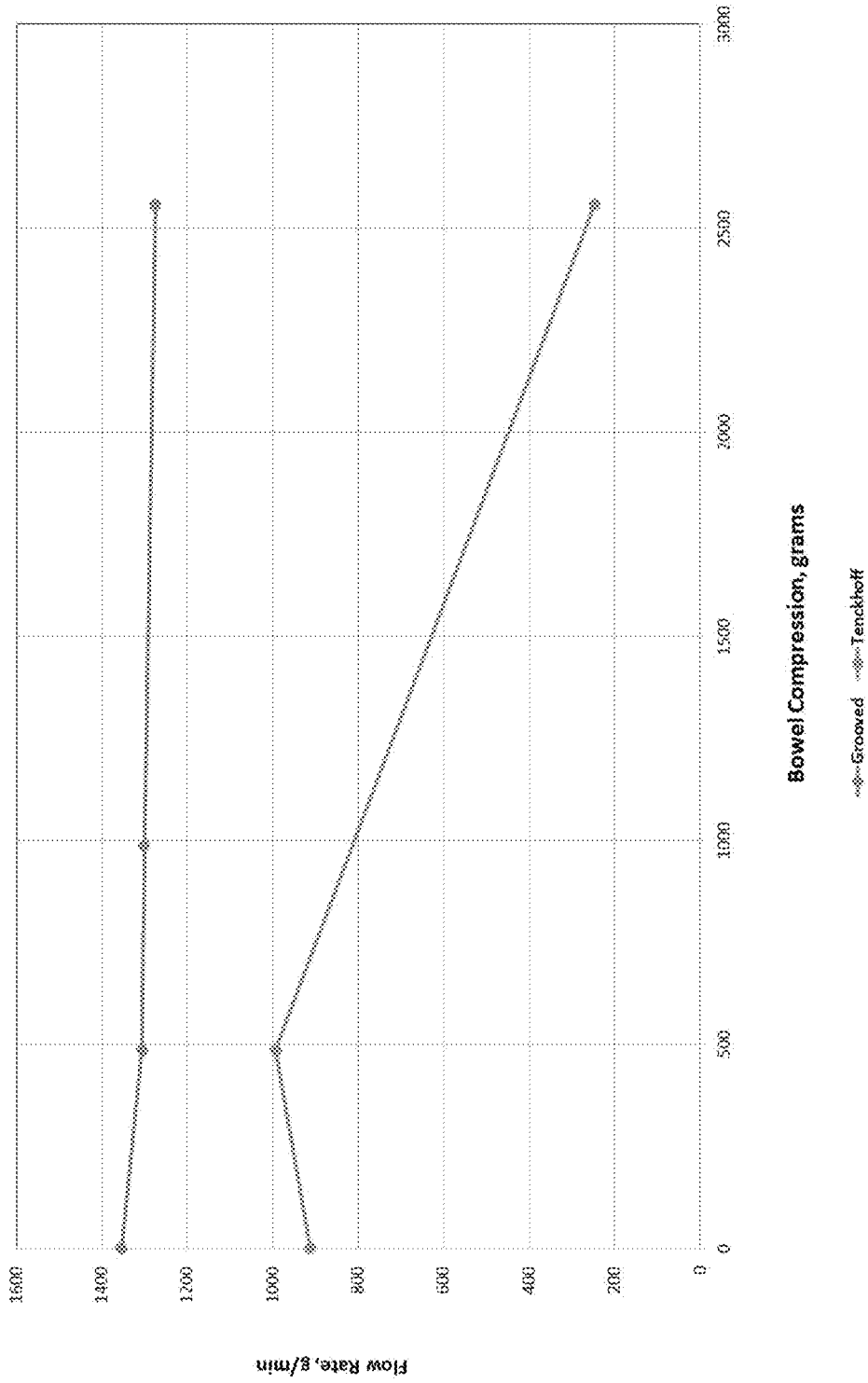
FIG. 16: Chart comparing results for Tenckhoff Free and Grooved catheters of the present embodiment, flow rate versus weight causing bowel compression.

As a summary, FIG. 16 shows the average flow rate of catheters in these experiments, graphed versus the weight placed above the cellulose tubes (simulated bowel loops). The average outflow rate was averaged from beginning of flow to the end of flow, so for Tenckhoff catheters the average flow value doesn't clearly display the decrease in flow that occurred near the end of outflow (when the flow rate reduced due to contact of the cellulosic tubings with the catheter). Nonetheless the results demonstrate that the Grooved catheter maintained high outflow values in spite of the presence of the simulated cellulosic tubes around it, and in spite of compression of the simulated bowel loops.

Figure 17:
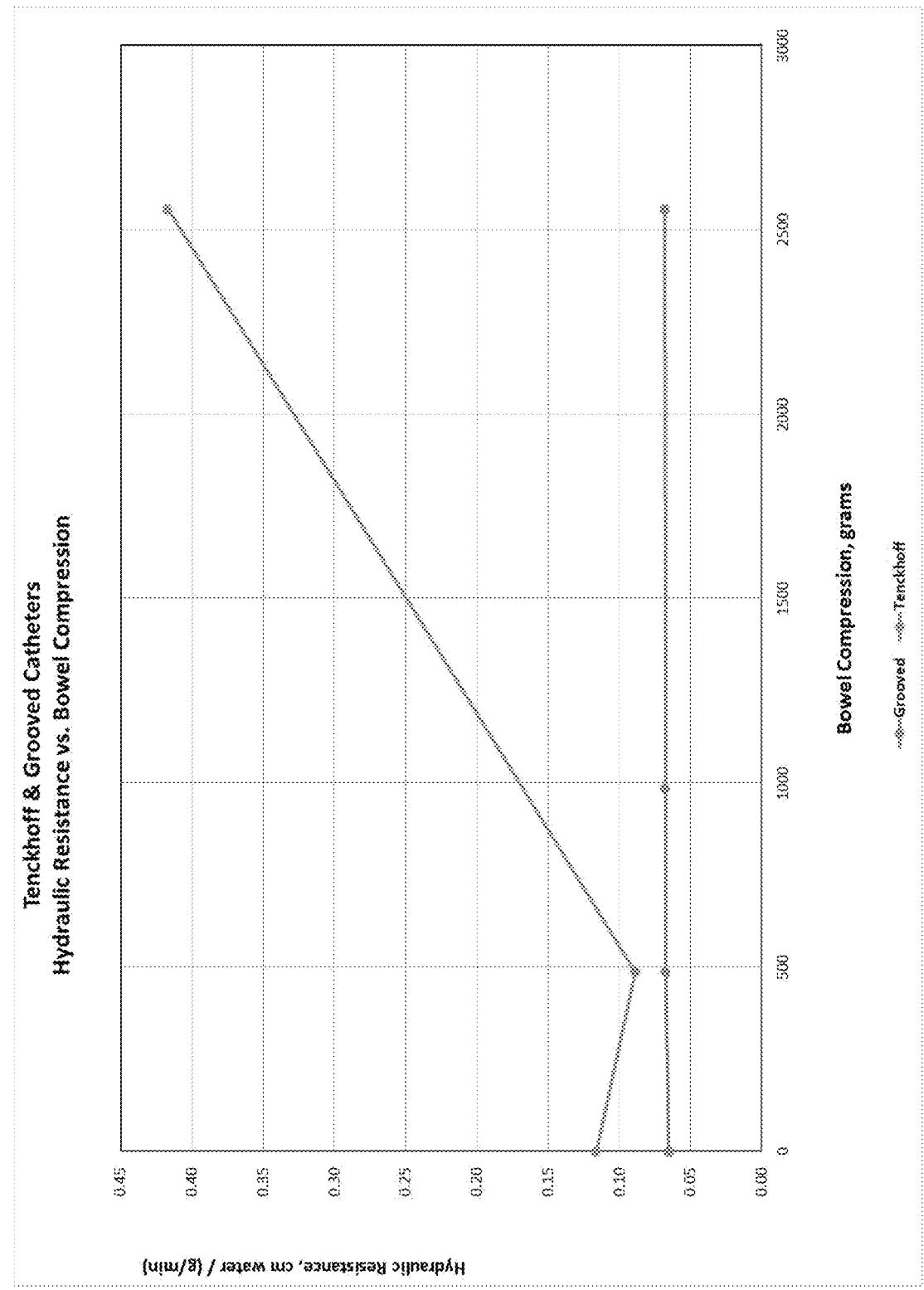
FIG. 17: Chart comparing results for Tenckhoff Free and Grooved catheters of the present embodiment, hydraulic resistance versus weight causing bowel compression.

The FIG. 17 shows the average hydraulic resistance of the catheters and associated vinyl tubing, versus the amount of weight which compressed the simulated bowel loops. It is apparent that the Grooved catheter has significantly less hydraulic resistance than the Tenckhoff catheter. The hydraulic resistance of the Tenckhoff catheter increases with increasing compression of the bowel loops (which brings the bowel loop surfaces closer to the catheter surfaces). The hydraulic resistance of the Grooved catheter is unaffected by this bowel compression.

CONCLUSION

This test model is a realistic simulation of the peritoneum during peritoneal dialysis. The Tenckhoff catheter in the model has an outflow pattern similar to the same catheter when used in peritoneal dialysis. Flow at the start of outflow is brisk, but as the peritoneal volume diminishes, the flow rate also diminishes. The catheter fails to drain all of the dialysate within the peritoneum, especially when the simulated bowel loops are compressed against the catheter. In contrast, in this model the Grooved catheter has outflow rate that is higher than the Tenckhoff, does not have a diminution of flow rate as fluid volume diminishes, and flow does not decelerate as the fluid volume diminishes.

Were we to use exactly the same Grooved catheter segment in patients as used in these experiments, it could deliver 2 liters per minute outflow rate with gravity drainage if the resistance of the subcutaneous tubing and machine tubing were low enough. This was demonstrated in the previous study of inflow flow rates. The model we plan to use clinically will have two to three times as many 0.5 mm diameter holes as the catheter tested in this study. With this change and with a low-resistance subcutaneous tubing segment, we expect the Grooved catheter to deliver the outflow rate needed for intraperitoneal hyperthermia (2 L/min). Importantly, it should be able to deliver this flow rate without need for a large intraperitoneal volume of fluid.

What is claimed is:

1. A catheter for fluid infusion and drainage comprising:
a non-cylindrical, slotted intraperitoneal tubing defining a first slot and a second slot wherein the first slot and the second slot has a narrow width to prevent ingress of abdominal contents or tissue, wherein the first slot and the second slot are between 0.5 to 1 mm wide and have a length more than twice the slot width to provide an area for fluid flow, wherein the non-cylindrical slotted intraperitoneal tubing has a non-cylindrical single interior opening large enough for unrestricted passage of fluid and a non-cylindrical exterior surface, wherein the slotted intraperitoneal tubing has a first exterior diameter, a first interior diameter, and a second interior diameter, wherein the first interior diameter is a distance between the furthest interior walls and the second interior diameter is the distance between a first trough portion and a second trough portion positioned opposite each other of the interior wall, wherein the first interior diameter is greater than the second interior diameter;
a flexible cylindrical tubing having a cylindrical interior surface having a first interior diameter and a cylindrical exterior surface having a first exterior diameter, wherein the flexible cylindrical tubing is formed in a reversibly bent orientation to form a single curvature having a single radius along a single plane, wherein an end of the flexible cylindrical tubing is attached to the non-cylindrical slotted intraperitoneal tubing; and
at least one cuff, wherein one of the at least one cuff is located at an apex of the single plane curvature at the flexible cylindrical tubing wherein the single plane curvature is between 150 to 180 degrees and wherein the at least one cuff is located at the apex of the curvature and is configured to hold and center the catheter at an abdominal musculature layer and fix the position of all components of the catheter, wherein the cylindrical slotted intraperitoneal tubing is configured to be fixed below the parietal peritoneum and an outer portion of the cylindrical tubing is configured to be fixed above the abdominal musculature;
wherein the non-cylindrical slotted intraperitoneal tubing has first exterior diameter is greater than the first exterior diameter of the flexible cylindrical tubing and the first interior diameter of the non-cylindrical slotted intraperitoneal tubing is equal to the first exterior diameter of the flexible cylindrical tubing, wherein a structure of the non-cylindrical slotted intraperitoneal tubing and a structure of the at least one slot are stabilized by the first trough the first slot and a second slot is stabilized by the second trough, wherein the at least the first slot and second slot extend for the length of the cylindrical slotted intraperitoneal portion of the catheter with holes for fluid passage in the bottom of each slot, wherein the holes are defined within the narrow width, wherein the holes are defined by each slot at a distance from the surface of the catheter, wherein the cylindrical tubing is coupled to the cylindrical slotted intraperitoneal tubing with an overmold component configured to maintain the connection between the flexible cylindrical tubing and the non-cylindrical slotted intraperitoneal tubing.

2. The catheter of claim 1, wherein the holes are circular.

3. The catheter of claim 2, wherein the non-cylindrical slotted intraperitoneal tubing is made by extrusion.

4. The catheter of claim 3, wherein the holes draining the bridging troughs are made by drilling, punching, or by pins during the extrusion process.

5. The catheter of claim 1, wherein the end of the cylindrical tubing is fastened to the middle of the cylindrical slotted intraperitoneal tubing, creating a T-shaped catheter to fix the position of all components of the catheter.

6. The catheter of claim 1, wherein the first exterior diameter of the non-cylindrical slotted intraperitoneal tubing is 8 mm and the first interior diameter of the non-cylindrical slotted intraperitoneal tubing is a maximum of 6 mm.

7. The catheter of claim 6, wherein the cylindrical slotted intraperitoneal tubing is approximately 13 cm to approximately 15 cm in length.

8. The catheter of claim 1, wherein at least one end of the cylindrical slotted intraperitoneal tubing is closed by either flattening the tubing and gluing a first side and a second side of at least one end of the cylindrical slotted intraperitoneal tubing together or fitting a molded silicone hemispherical piece to at least one end of the cylindrical slotted intraperitoneal tubing.

9. The catheter of claim 1, wherein the non-cylindrical slotted intraperitoneal tubing has at least one closed end.

10. The catheter of claim 6, wherein the first exterior diameter of the cylindrical tubing is 6 mm and the first interior diameter of the cylindrical tubing is 4 mm.

11. The catheter of claim 1, wherein the cylindrical tubing is fastened to the cylindrical slotted intraperitoneal tubing with an overmold, wherein the non-cylindrical exterior surface provides greater surface area for flow to lower velocity of the fluid at any given outflow or inflow rate.

12. The catheter of claim 1, wherein the end of the cylindrical tubing is attached to an end of the cylindrical slotted intraperitoneal tubing, wherein the curvature includes a portion of the cylindrical tubing, creating a catheter which can be made to be linear with an internal stylet.

13. A catheter for fluid infusion and drainage comprising:
a slotted tubing, the slotted tubing defining at least one slot wherein the at least one slot has a length more than twice the at least one slot's width, wherein the slotted tubing has a non-cylindrical interior opening, wherein the non-cylindrical interior opening has a first interior diameter and second interior diameter located between a first trough and a second trough positioned opposite the first trough;
a cylindrical tubing, the cylindrical tubing flexible and configured to be reversibly bent to form a single plane curvature, wherein the single plane curvature can be made to be linear, wherein the cylindrical tubing has first exterior diameter and first interior diameter, wherein the first exterior diameter is equal to or greater than the first interior diameter of the non-cylindrical interior opening; and
at least one cuff, wherein one of the at least one cuff is located at an apex of the single plane curvature at the cylindrical tubing and wherein the one of the at least one cuff located at the apex is configured to be positioned within the abdominal musculature layer;

wherein an end of the cylindrical tubing is attached to the slotted tubing.

* * * * *